United States Patent [19]

Haeussinger

[11] 4,216,556

[45] Aug. 12, 1980

[54] EXTRICATION SPLINT FOR ACCIDENT VICTIMS

[76] Inventor: John D. Haeussinger, 9566 Halberns Blvd., Santee, Calif. 92071

[21] Appl. No.: 950,132

[22] Filed: Oct. 10, 1978

[51] Int. Cl.² ............................................. A61G 7/10
[52] U.S. Cl. .......................................... 5/82 R; 5/114
[58] Field of Search .................... 5/81 R, 82 R, 82 B, 5/114

[56] References Cited

U.S. PATENT DOCUMENTS

| | | | |
|---|---|---|---|
| 2,614,266 | 10/1952 | Smith | 5/82 |
| 3,139,883 | 7/1964 | Collins | 5/82 |
| 3,373,454 | 3/1968 | Curtis | 5/82 |
| 3,574,871 | 4/1971 | Greene | 5/81 R |
| 3,663,972 | 5/1972 | Denton | 5/82 |
| 3,921,231 | 11/1975 | Bourgraf et al. | 5/82 |
| 4,127,120 | 11/1978 | Applegate | 5/82 |

Primary Examiner—Casmir A. Nunberg

[57] ABSTRACT

An extrication splint for injury victims is provided which is assembled beneath the victim at the accident site and assumes the contour of the victim so that he need not be extended into lying position in order to fit on a conventional gurny. The structure consists of a plurality of cross-bars which are slid beneath the victim who may be, for example, in an automobile seat, and a pair of parallel siderails having several jointed segments to accommodate natural bends in the body are assembled to the cross-bars on each side of the victim subsequent to which the rail joints are tightened and the victim is removed on a rigid structure.

7 Claims, 5 Drawing Figures

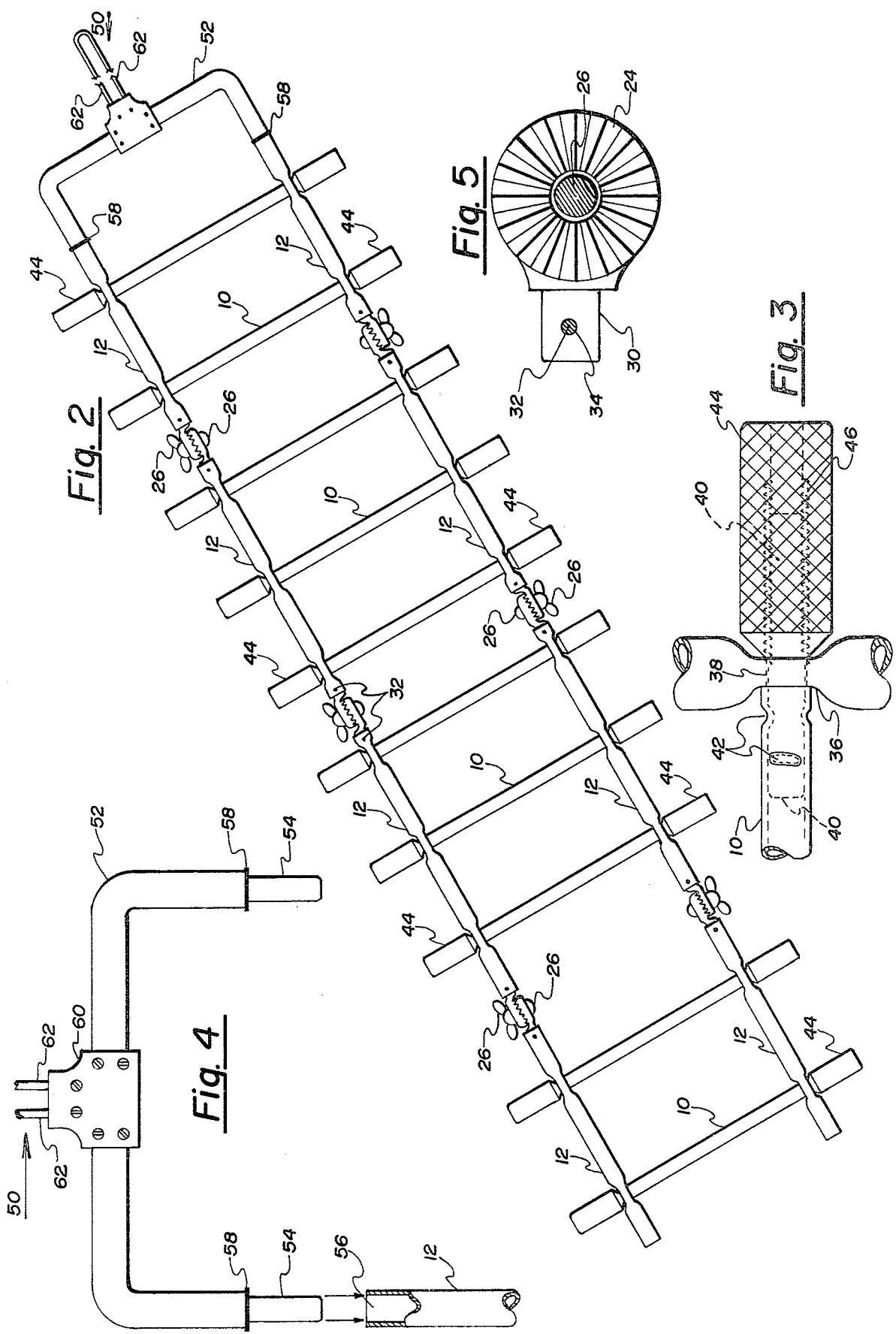

EXTRICATION SPLINT FOR ACCIDENT VICTIMS

BACKGROUND OF THE INVENTION

In many instances, especially when police, firemen and ambulance operators are called upon to remove victims from automobile accidents, fires and other accidents, it is necessary to transport the victim to a hospital or the like and it is preferable in the interest of risking the least amount of additional injury that his body be maintained substantially in the orientation in which it was found at the accident scene until securely in a hospital and under a doctor's care.

Conventional extrication means widely used by police and the like involves the utilization of a simple slab of plywood which is slid beneath the body of the patient in order to extricate him from a tight place, typically the front seat of a vehicle which has had the top or front portion crushed around him. Once the victim is somehow slid out of his entrapping circumstances, typically he is then stretched horizontally into the lying position on a carrying stretcher, termed a gurny.

The combination of the extrication procedure in which the only body-supporting member is a section of plywood, and the subsequent forcing of the body into the prostrate position so that it fits existing equipment runs substantial risk of further injuring the victim by causing previously broken bones to work themselves through more tissue, and otherwise jostling injured portions of the body.

Another problem area in the transportation of accident victims lies in the movement of especially fire victims out of old hotels and other buildings having narrow staircases, perhaps with numerous hairpin turns. Because the conventional gurny will not fit through these stairways, the accepted way of extricating the victim is by searching for some kind of chair, which may not be in much better shape than the victim. A pair of rescuers attempt to find some convenient place on the chair to grip and try to negotiate down the stariway without catapulting the victim head-first down the stairwell while strapped to a chair.

SUMMARY OF THE INVENTION

The present invention provides a plurality of slats or cross-bars which are inserted beneath the major body portions of the victim, and a pair of segmented siderails having joints corresponding to the positions of the knees, hips and upper back are laid on each side of the victim and the cross-bars are thence secured to the siderails by members which act also as handles.

Several Velcro straps are applied across the front of the body of the victim, and an optional head-engaging member utilizing a chin strap may be mounted to the top of the siderails. The joints in the siderails are tightened to maintain the entire structure rigid after the cross-bars have been secured, and the entire structure having the victim's body thereon is transported to the hospital.

Because of the rigidly tightenable joints provided in the siderails, the unit can be formed in the shape of the traditional chair utilized in small stairways but has the advantage of providing more support and particularly providing a better method of gripping to the rescuing personnel.

BRIEF DESCRIPTION OF THE DRAWINGS

FIG. 2 is a top elevation view of the splint completely extended;

FIG. 3 is a detailed view showing the cross-bar attachment to the side rail;

FIG. 4 is a detailed view of the removable chin strap support structure;

FIG. 5 is a front elevation view of a radial detent used in the joints showing the section of a connecting bolt in the center thereof.

DETAILED DESCRIPTION OF THE PREFERRED EMBODIMENT

Figure 1:
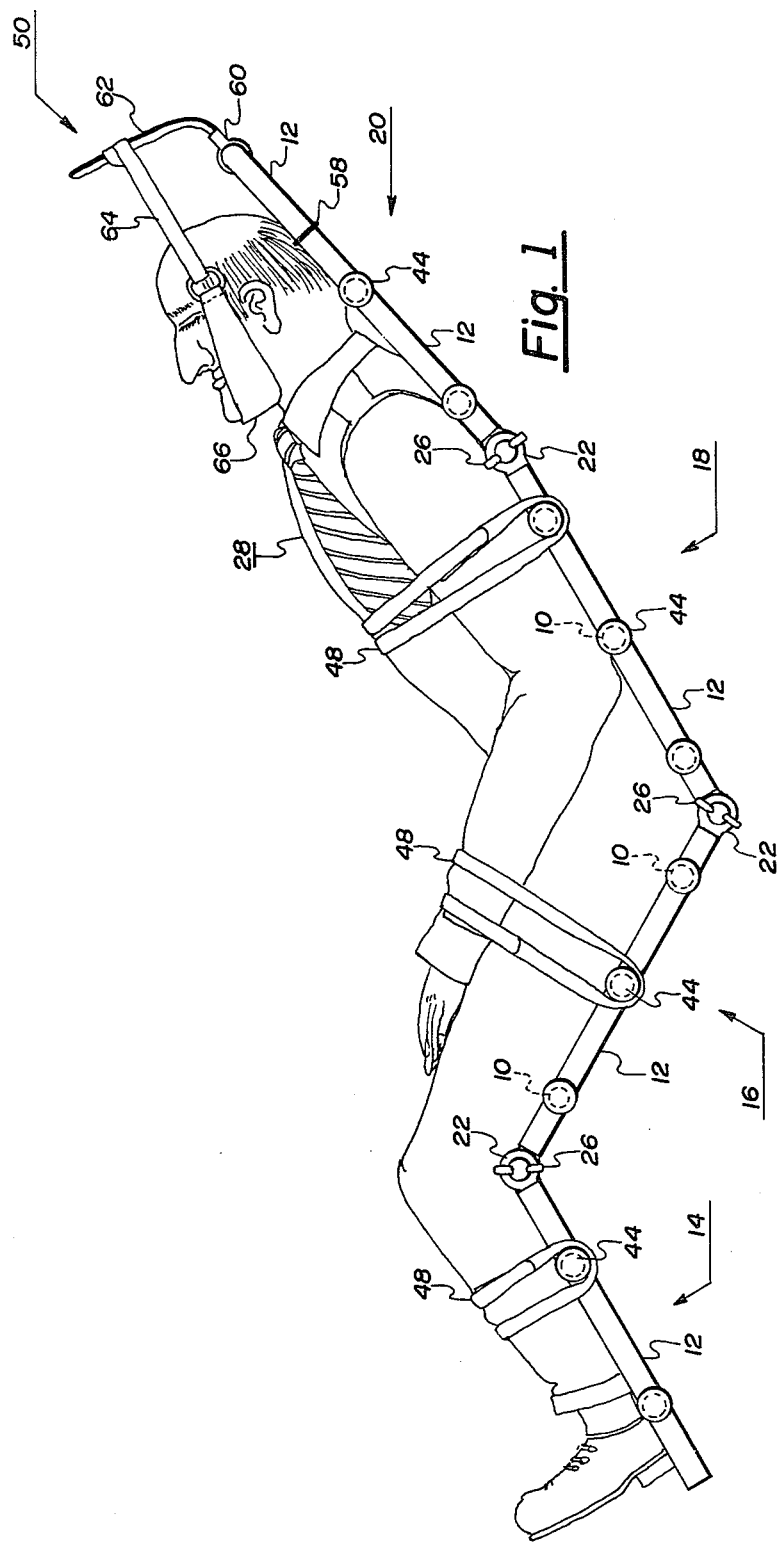
FIG. 1 is a side elevation view of the splint in use with a patient strapped thereto.

The invention is simple in concept and involves a number of crossbars 10 which are releasibly connected in parallel fashion orthogonally to side rails 12. The side rails 12 are each provided in four distinct segments 14, 16, 18 and 20 and these segments are joined together by pivotal means capable of being secured in any one of numerous angular positions. This structure is shown at 22 joining adjacent segments of the side rails, and each of these joints is comprised of a pair of radial detent half plates 24, one of which is illustrated in FIG. 5, which are secured together by bolt and wing nut structure 26. Thus it can be seen from FIGS. 1 and 2 that by loosening the wing nuts and thus freeing, or at least easing the tension on the radial detent half plates, any of the side rail segments can be moved to strike a different angle with adjacent segments, subsequent to which a rigid structure is achieved again by retightening the wing nuts.

The result of this is seen in FIG. 1 wherein the body of a patient 28 is strapped to the splint such that his knees, waist, and middle to upper back are adjacent the joints provided in the side rails so that the splint conforms more or less to the configuration of the body.

In the embodiment shown, both the crossbars and side rails are made of tubular aluminum, and the half plates 24 each have a plug 30 which fits into the open end of the respective segment and is retained by a pin 32 passing through a bore 34 in the plugs, which of course mates with appropriate holes in the side rail structure.

At intervals the side rails are constricted as at 36 and provided with a bore shown in FIG. 3 at 38 in the restricted portions to permit the passage therethrough of the threaded shafts 40 which are crimped at 42 into the pins of the aluminum crossbars 10. These threaded shafts pass through the bores 38 and are retained by means of handles 44 having a threaded socket 46 to engage the shafts 40.

As can be seen from FIG. 1, the combination handle, crossbar retainers 44 are also used as anchors for support straps 48 which can be positioned at any convenient pair of the handles 44 to capture the body 28 of the accident victim. It is possible that a strap be used for every pair of handles, although in all likelihood a smaller number would be sufficient.

As can be seen in FIGS. 1, 2 and 4, a support structure 50 is provided having a yoke-like crossbar 52, also of tubular aluminum which has a pair of plugs 54 extending from the open ends which removably seat in open top ends 56 of the side rails. A pair of washers 58 may be provided at this juncture to ensure a positive mating of two parts.

This yoke has a bracket 60 mounted to the middle thereof from which extends a member 62 which in the preferred embodiment is a loop of somewhat resilient, malleable wire, the tip end of which is adapted to engage a strap 64 connected to a chin cup 66. Once the patient is secured to the splint, the chin strap and cup may be added if desired and the wire loop 62 bent backwards to establish the proper degree of restraining force or traction on the chin of the patient. Although a wire loop as shown is a simple and effective way of providing the chin strap retainer, it is certainly not the only means available to accomplish this end, and is not intended to be limiting.

The principal advantages of the invention are two. First, it can be seen that the entire structure can be disassembled and would ordinarily be provided in disassembled form. In this condition, it would occupy an absolute minimum of space in an emergency vehicle or elsewhere in an environment ordinarily requiring the stretcher or gurny.

However, the principal advantage lies in the method by which the splint is used to extricate the body of an accident victim. The splint is literally assembled around, or beneath, the body of the victim, first by inserting the crossbars beneath the various portions of the victim's body, such that the victim is not disturbed in more than a very minor fashion.

Once an adequate number of crossbars are inserted (which need not be the entire amount, and need not represent all of the four segments of each rail provided), the side rails are positioned on each side of the victim's body and the crossbars are passed through the side rails into engagement therewith, and locked in position by engaging the handles 44 on the threaded shafts of the crossbars.

The side rails may have been connected to the crossbars as individual segments, or in one piece with the joints 22 loose. In either event, the next step would be to secure the joints 22 by passing the bolts and wing nuts 26 through the mating half plates 24 is they have not already been joined, or merely tightening the wing nuts if they have. Once the wing nuts are tightened, a rigid, but probably non-planar splint is defined conforming to the underside of the patient's body.

Subsequent to making the splint rigid, a number of the straps 48 are secured to the handles 44 and across the victim's body. At this point the body is secured rigidly in a position very similar to that in which the body was originally found. It can now be extricated from the accident scene, or if it is felt to be necessary the chin support structure 50 together with the chin strap and chin cup can be added to provide traction, or at least support for the victim's head.

Clearly numerous other ways of providing the crossbars, which could be thin and slatted rather than circular aluminum tubing, could be conceived within the spirit of the invention. Likewise, there is room for entertaining a variety of ideas regarding the construction of the side rails 12 and particularly the means by which the crossbars are connected to the side rails. It is conceivable for instance that the side rails could be snapped on the crossbars laterally rather than having to be inserted over the tips of the shafts. This would facilitate the rapid connection of these parts together. Also, it is conceivable that a structure integral to the ends of the crossbars or to the side rails could be provided for joining the two parts, so that loose handles 44 would not be necessary, and thus the chance of losing them would be obviated.

It is the essense of the invention that a splint is provided in parts which are assembled beneath the victim's body and in the position in which it is found, and that the splint is subsequently made rigid in this position to expedite removal of the body and to ensure that portions of the body are not exposed to a risk of injury prior to arriving at the hospital due to reorienting the body portions, or due to extricating the body for example from the front seat of a vehicle by a crude method such as sliding a plywood board beneath a portion of the body and tugging on several parts of the body at once.

I claim:

1. An extrication splint for injury victims comprising:
    (a) a pair of spaced siderails each being provided in at least two jointed segments and the joints connecting said segments having means to rigidly fix same at any one of several angles;
    (b) a plurality of cross-bars separate from said siderails;
    (c) means to releasibly mount said cross-bars to and between said siderails to support a victim's body thereon and
    (d) a plurality of longitudinally spaced handles projecting laterally from each side of said splint.

2. A splint according to claim 1 wherein said cross-bars each has a central portion and ends defining shafts, and said means to releasibly mount said cross-bars comprise spaced holes in said siderails to receive said shafts, said shafts are threaded and said handles have threaded bores to threadedly receive said shafts and serve as retainers holding said cross-bars and rails together.

3. A splint according to claim 1 and including a plurality of straps having Velcro fasteners on the ends thereof and being dimensioned to be engaged around a plurality of said handles and the body of a victim to secure said straps to engage a victim on said splint.

4. A splint according to claim 1 wherein said siderails are of tubular construction and each has an open head end defining a socket and including a removable bracket having a chin strap thereon and having two spaced projections to fit said sockets for mounting same to said head ends of said siderails.

5. Structure according to claim 4 wherein said bracket includes a maleable wire projection and is adjustable by virtue of being bendable to different positions and to adjust the tension on said chin strap.

6. A method of deploying an extrication splint beneath an injury victim comprising:
    (a) inserting a plurality of separate cross-bars laterally beneath the body of the victim;
    (b) positioning a pair of siderails provided in a plurality of segments connected by joints having means to rigidly fix said joints alongside said victim;
    (c) fastening said cross-bars to said siderails; and
    (d) rigidly fixing said joints to maintain said segments in rigid alignment with the body of the victim.

7. A method according to claim 6 wherein said siderails are provided in a plurality of segments connected by joints having means to rigidly fix said joints, and including the further step of:
    (a) rigidly fixing said joints to maintain said segments in rigid alignment with the body of the victim.

* * * * *